(12) United States Patent
Okabe et al.

(10) Patent No.: US 7,446,864 B2
(45) Date of Patent: Nov. 4, 2008

(54) DEFECT INSPECTION METHOD AND DEFECT INSPECTION SYSTEM USING THE METHOD

(75) Inventors: Hiroshi Okabe, Kyoto (JP); Toshihiko Matsumoto, Kyoto (JP)

(73) Assignee: Omron Corporation, Kyoto-Shi (JP)

( * ) Notice: Subject to any disclaimer, the term of this patent is extended or adjusted under 35 U.S.C. 154(b) by 0 days.

(21) Appl. No.: 11/398,763

(22) Filed: Apr. 6, 2006

(65) Prior Publication Data

US 2006/0251315 A1 Nov. 9, 2006

(30) Foreign Application Priority Data

Apr. 8, 2005 (JP) ............................ P2005-111536
Mar. 8, 2006 (JP) ............................ P2006-062505

(51) Int. Cl.
*G01N 21/00* (2006.01)
(52) U.S. Cl. .................................... 356/237.1
(58) Field of Classification Search ............... 356/237.1
See application file for complete search history.

(56) References Cited

U.S. PATENT DOCUMENTS 5,982,493 A * 11/1999 Lehnen et al. ............... 356/613
6,064,478 A * 5/2000 Paul et al. ................. 356/237.1
6,222,624 B1 * 4/2001 Yonezawa ................. 356/237.1
6,668,078 B1 * 12/2003 Bolle et al. .................. 382/164
6,928,185 B2 * 8/2005 Yonezawa ................... 382/149
7,027,640 B2 * 4/2006 Park et al. ................... 382/152
2001/0000679 A1 * 5/2001 Vaez-Iravani et al. .... 356/237.1

FOREIGN PATENT DOCUMENTS

| EP | 0 452 905 | 10/1991 |
|---|---|---|
| EP | 1 408 326 | 4/2004 |
| JP | 62-038348 | 2/1987 |
| JP | 01-113639 | 5/1989 |
| JP | 2000-009591 | 1/2000 |
| JP | 2003-075363 | 3/2003 |
| JP | 2004-184241 | 7/2004 |
| WO | WO-01/01118 | 1/2001 |
| WO | WO-01/49043 | 7/2001 |

* cited by examiner

*Primary Examiner*—Tarifur R. Chowdhury
*Assistant Examiner*—Isiaka O Akanbi
(74) *Attorney, Agent, or Firm*—Foley & Lardner LLP

(57) ABSTRACT

A surface of a work to be inspected is irradiated with an illumination unit for a coaxial incident illumination and an illumination unit for an oblique incident illumination driven to take its image by a camera at the same time. Each of the illumination units and comprises light sources emitting color lights R, G and B, respectively. One of the three kinds of light sources is lighted in the illumination unit and one or two of the light sources which are not lighted in the illumination unit are lighted in the illumination unit.

6 Claims, 14 Drawing Sheets

Fig. 4

| Object to be detected | Irregular defect on coating layer surface |||
|---|---|---|---|
| Case | A | B | C |
| Principle of detection | Defect is detected as dark region | Defect is detected as dark region | Defect is detected as bright region |
| Undetectable defect | | | |

Fig. 5

| Object to be detected | | | Color defect | | | |
|---|---|---|---|---|---|---|
| Case | D | E | F | G | H (Beyond assumption) |
| Principle of detection | Defect is detected as dark region | Defect is detected as bright region | Defect is detected as dark region | Defect is detected as dark region | Defect is detected as bright region |

Fig. 6

| Illumination method | Coaxial incident illumination | Oblique incident illumination | |
|---|---|---|---|
| Detectable defect | Defect on coating layer surface (irregular defect and color defect) | • Inner color defect (dark)<br>• Defect on coating layer surface (dark) | • Inner color defect (bright)<br>• Defect on coating layer surface (bright) |
| Illumination light suitable for detection | Color in complementary relation with color of work body | Same color as color of work body | Color in complementary relation with color of work body |
| When work body is white | White, R, G, B | White (RGB) | White (RGB) |
| When work body is gray | White, R, G, B | White (RGB) | White (RGB) |
| When work body is yellow | Blue (B) | Yellow (RG) | Blue (B) |

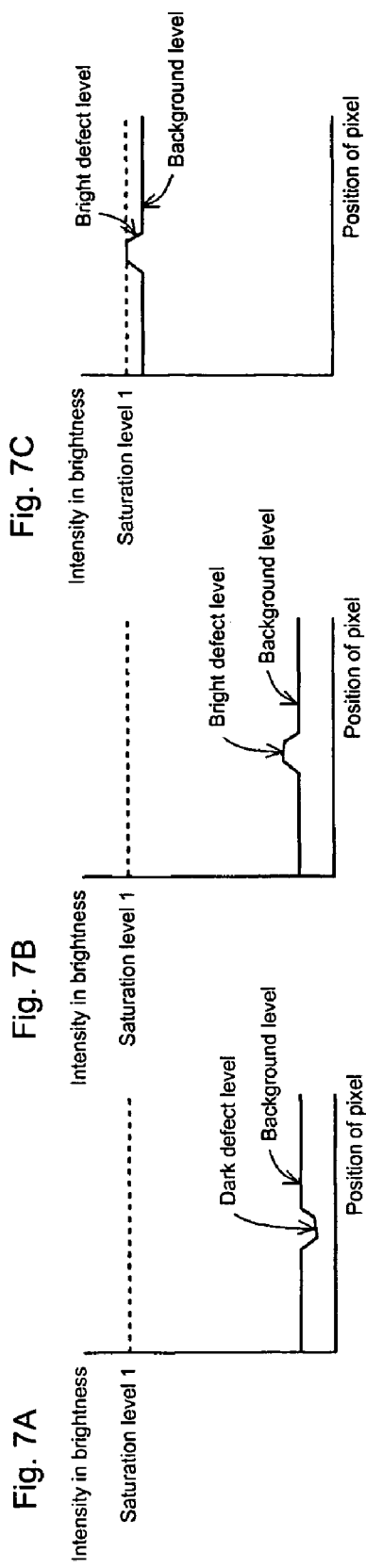

Fig. 9

| Color of work body | Illumination color / Reflection kind | Coating layer | | Work body | |
|---|---|---|---|---|---|
| | | Regular reflection | Diffused reflection | Regular reflection | Diffused reflection |
| White | R, G, B | 3.5 | 0 | 0.2 | 1 (Reference for standardization) |
| Gray | R, G, B | 3.5 | 0 | 0.4 | 0.5 |
| Yellow | R | 3.5 | 0 | 0.3 | 1.1 |
| | G | 3.5 | 0 | 0.3 | 0.5 |
| | B | 3.5 | 0 | 0.3 | 0.2 |

Fig. 10

< Method 1 >

|  | Illumination method | Illumination color |
|---|---|---|
| First imaging | Coaxial incident illumination | Any color (including white) |
| Second imaging | Oblique incident illumination | Color (including white) according to work body |

< Method 2 >

|  | Illumination method | Illumination color |
|---|---|---|
| Only one imaging | Coaxial incident illumination | Any color (including white) |
| | Oblique incident illumination | Color (including white) according to work body |

< Method 3 >

|  | Illumination method | Illumination color |
|---|---|---|
| Only one imaging | Coaxial incident illumination | Any one of R, G and B |
| | Oblique incident illumination | Combination of two colors except for that selected in the coaxial incident illumination |

Fig. 11

| | | Color of work body | | | | | | | | |
|---|---|---|---|---|---|---|---|---|---|---|
| | | White or silver | | | Yellow | Blue | Green | | Red | |
| Coaxial incident illumination | R | | | O | | O | | | | |
| | G | O | | | | | | O | | O |
| | B | O | O | | | | | O | O | O |
| Oblique incident illumination | R | | O | | O | | | | | |
| | G | | | O | O | O | | O | O | O |
| | B | | O | O | O | O | | O | O | O |
| Undetectable defect color | | Yellow | Red purple | Blue green | White | Red purple | Yellow | Cyan | Yellow | Red purple |

Fig. 14
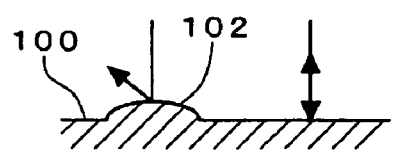
Fig. 15
(1)  (2)
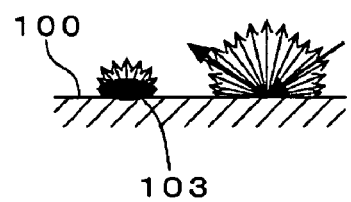 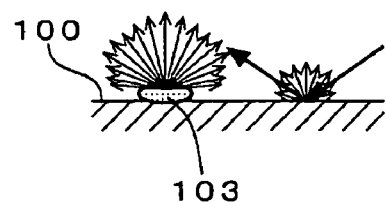

DEFECT INSPECTION METHOD AND DEFECT INSPECTION SYSTEM USING THE METHOD

This application claims priority from Japanese patent applications JP P2005-111536, filed on Apr. 8, 2005, and JP P2006-062505, filed on Mar. 8, 2006. The entire contents of each of the aforementioned applications are incorporated herein by reference.

BACKGROUND OF THE INVENTION

1. Field of the Invention

The present invention relates to a technique for inspecting whether an irregular defect or a color defect is generated on a surface of an object to be inspected which is formed of a material having a high regular reflectance (a resin, metal or the like).

2. Description of the Related Art

It is very important for a product which places a particular emphasis on its design such as a car or a home appliance to have no irregularity in luster or color on its surface in view of enhancing its commercial value.

Although a surface of such product is made of a colored resin or metal, the surface could have an irregular defect or a color defect.

The irregular defect is generated when the surface is protruded or recessed caused by a manufacturing defect. The irregular defect includes a scratch generated after manufactured. The color defect is generated when a peripheral coating material is attached on the surface at the time of manufacturing.

As a method of detecting the above defect by using an image processing method, Japanese Unexamined Patent Publication No. 2003-75363 discloses that a surface of an object to be inspected (referred to as the "work" hereinafter) is irradiated with a coaxial incident illumination and an illumination from an oblique direction, and a first imaging device for taking an image of a regularly reflected light from the work with respect to the coaxial incident illumination, and a second imaging device for taking an image of a diffused reflected light from the work with respect to the illumination from the oblique direction are provided. In addition, an irregular defect on the surface of the work is detected using the image generated by the first imaging device, and a color defect on the surface of the work is detected using the image generated by the second imaging device.

However, according to the method in Japanese Unexamined Patent Publication No. 2003-75363, since the two imaging devices are provided, the cost becomes high. In addition, they occupy a large space in an optical system, and control for the imaging devices individually is complicated.

Furthermore, according to Japanese Unexamined Patent Publication No. 2003-75363, the cylindrical work to be inspected is rotated and each imaging device takes an image of an entire periphery of the work, and each region whose image is to be taken is sequentially irradiated with two kinds of illuminations. According to this method, a processing time is long, so that many works cannot be processed efficiently.

SUMMARY OF THE INVENTION

The present invention was made in view of the above problem and it is an object of the present invention to be able to detect both irregular defect and color defect on a surface of an object to be inspected by taking an image of the object at one time.

According to a defect inspection method and a defect inspection system of the invention, it is inspected whether the defect is generated or not on the surface of the object formed of a predetermined material.

The above material may be a material having a high regular reflectance such as a resin or metal. In addition, this material may be colored with a coating material or uncolored like metal. Furthermore, after the object is manufactured, a coating film (which is not transparent but has a high regular reflectance) is attached on its surface in some cases.

A defect inspection method according to the present invention comprises a step of setting an imaging device for generating a color image so that a regularly reflected light from the object to be inspected is inputted thereto when the object is irradiated from a predetermined direction; a step of taking an image of the object by the imaging device with a first illumination for irradiating the object with any one of three kinds of lights R, G and B from the predetermined direction and a second illumination for irradiating the object with one or two kinds of lights which are not used in the first illumination from a direction oblique to an optical axis of the imaging device at the same time; and a step of detecting an irregular defect and a color defect on the surface of the object using a color image provided at the imaging step.

In addition, the colors R, G and B correspond to image data generated by the imaging device for forming a color image and R designates red, G designates green, and B designates blue in general.

According to the above method, an optical axis of the imaging device is set so as to be perpendicular to a surface of the object, the first illumination is applied along the optical axis of the imaging device (coaxial incident illumination) and the second illumination is applied to the surface of the object from an oblique direction (referred to as the "oblique incident illumination" hereinafter). When the surface of the imaging region is not flat, the optical axis of the imaging device may be set so as to be perpendicular to a tangent line with respect to a predetermined position (central position, for example) in the imaging region.

However, the arrangement of the optical system is not limited to the above. For example, the first illumination may be applied to the surface of the object from the oblique direction and the optical axis of the imaging device may be set such that the imaging device can receive the regularly reflected light of the illumination light.

According to the above method, although the regularly reflected light of the first illumination from the surface of the object enters the imaging device, in case that there is an irregular defect on its surface, the regularly reflected light from the defect travels in a different direction. Thus, when an image of the reflected light of the first illumination from the object is taken, the irregular defect appears as a dark region on the image as compared with the other part.

According to the second illumination, the light reflected along the optical axis of the imaging device among the diffused reflected light from the surface of the object enters the imaging device. Since the color defect is a region having a color different from the other part, its diffused reflectance is also different from that of the other part. Thus, when an image of the diffused reflected light of the second illumination from the object is taken, the color defect appears as a dark or bright region on the image as compared with the other part.

According to the above method, when the first and second illuminations are applied at the same time, one kind of light of the colors R, G and B is used in the first illumination and one or two kinds of lights which are not used in the first illumination are used in the second illumination. Since even the all-purpose imaging device has a function to divide the light to imaging elements corresponding to the colors R, G and B when it receives the light, the image of the color (R, for example) corresponding to the first illumination reflects the regularly reflected light from the object, and the image of the color (G and B, for example) corresponding to the second illumination reflects the diffused reflected light from the object. Thus, even when both irregular defect and color defect exist on the surface of the object, the image in which both defects can appear as regions different from the normal part can be provided at one imaging operation.

In addition, both illuminations can be performed at the same time to generate the image in which the two kinds of defects can be detected even by using the same color light (white light, for example). However, since the brightness of the generated image is the sum of the brightness of the reflected lights corresponding to the two kinds of illuminations in this case, when the intensity of each illumination is raised, the brightness on the image could be saturated. In this case, it is difficult to adjust the intensity of each illumination so that the defect can be stably detected.

Meanwhile, according to the present invention, since the different color is used in the illumination and each image data reflects the reflected light of either one of the illuminations, the intensity of each illumination can be adjusted so as to be suitable for the detection of each defect. Thus, both irregular defect and color defect can be detected with high precision.

To detect the defect in the above method, it is preferable that an image of a non-defective model is taken previously under the same condition as that in the inspection process and the image is registered as a model image and differential arithmetic processing between the color image of the inspected object and the model image is performed.

According to the preferred embodiment of the above method, at least one illumination color of the first illumination and the second illumination is variable. Thus, the defect inspection can correspond to the color of the object and the color of the defect part.

According to a more preferable inspection process, the color image provided at the imaging step is cut into an image having a color corresponding to an illumination color of the first illumination and an image having a color corresponding to an illumination color of the second illumination, and the irregular defect is detected using the former image while the color defect is detected using the latter image. Thus, since the image with respect to the first illumination and the image with respect to the second illumination are separately processed, the kind of the defect can be specified.

In addition, according to the color defect detection with the second illumination, illumination color of the defective part could be the similar to that of the non-defective part on the image in case of a particular illumination color. Thus, the light color used in the second illumination may be selected according to the color of the object or the defect color which could appear on the image, and the other color light may be used in the first illumination. Alternatively, a light color which suppresses the diffused reflected light is selected for the first illumination according to the color of the object and the other color light may be selected for the second illumination.

According to a preferred embodiment of the above method, a non-defective model of the object to be inspected is irradiated with the first and second illuminations at the same time and intensity of a light source used for each illumination or sensitivity of the imaging device is adjusted so that brightness of an image provided from the imaging process may reach a predetermined target level, prior to inspection.

Since the non-defective model has no defect, it can be considered that the brightness of the image provided by taking the image of the model is the brightness of the background of the defect. Here, in a case where the defect on the image appears as the dark region as compared with the other part, when the brightness level of the background is too low, it is difficult to discriminate the defect from the background. Meanwhile, in a case where the defect on the image appears as the bright region as compared with the other part, when the brightness level of the background is too high, the brightness of the defect is saturated and it is difficult to recognize the difference between the defect and the background.

The present invention described above was made in view of the above problem. Thus, when the background level is adjusted using the non-defective model previously, in case that there is a defect in the inspected work, it is possible to generate the image in which the defect can be clearly recognized as a region having a different brightness. In addition, since the reflected light image with respect to the first and second illuminations can comprise images corresponding to the respective illumination colors, when the image is taken with two kinds of illuminations at the same time and the image of each color is adjusted so as to reach each appropriate level, the image having a brightness level suitable for inspection can be provided in each of the irregular defect and color defect.

A defect inspection system according to the present invention comprises a first illuminating device for illuminating the object to be inspected from a predetermined direction; an imaging device arranged so as to receive a regularly reflected light from the object under an illumination by the first illuminating device to thereby generate a color image; a second illuminating device for illuminating the object from an oblique direction with respect to an optical axis of the imaging device; a control device for controlling illumination operations of the first and second illuminating devices and operating the imaging device under illuminations of the first and second illuminating devices; a detecting device for detecting an irregular defect and a color defect on a surface of the object using a color image generated by the imaging device controlled by the controlling device; and an output device for outputting a result detected by the detecting device.

The first and second illuminating devices each comprise three kinds of light sources which emit colors R, G and B, respectively. In addition, the control device lights one of the three kinds of light sources in the first illuminating device and lights one or two kinds of light sources which are not lighted in the first illuminating device, in the second illuminating device.

According to the above, a plurality of light sources such as LED can be provided for each of the colors R, G and B in each of the first and second illuminating devices. In addition, a half mirror and the like may be provided in the first illuminating device to conform the optical axis of the illumination light to the optical axis of the imaging device.

The control device and detecting device each comprise a computer in which a program to carry out the process of the device is stored, for example. The output device comprises a device (monitor, for example) to display the result detected by the detecting device and a device to output information showing the detected result to an external device (an "OK" signal may be outputted when there is no defect and a "NG" signal may be outputted when there is a defect, for example). When the detected result is displayed, the image may mark the detected defect on the work.

According to one preferred embodiment of the defect inspection system, an illumination light color of at least one of the first illuminating device and the second illuminating device is variable. In this embodiment, the defect inspection can correspond to the color of the object and the color of the defect part.

In addition, according another preferred embodiment, the detecting device cuts the color image generated by the imaging device into an image having a color corresponding to the light source lighted in the first illuminating device, and an image having a color corresponding to the light source lighted in the second illuminating device, and the irregular defect is detected using the former image while the color defect is detected using the latter image. In this embodiment, the irregular defect and the color defect on the surface of the object can be separately detected.

The defect inspection system according to another embodiment further comprises an adjusting device for adjusting a light amount of each light source of the first and second illuminating devices or sensitivity of the imaging device for the colors R, G and B individually; and a memory for storing an adjustment value of the adjusting device required for bringing brightness of the image generated by the imaging device to a predetermined target level. In addition, the control device applies information stored in the memory to the adjusting device to adjust the light amount of each light source or the sensitivity of the imaging device.

According to the defect inspection system in the above embodiments, since the appropriately adjustment value is registered in the memory prior to inspection, the illumination light amount or sensitivity of the imaging device is automatically adjusted at the time of inspection and the image having brightness suitable for detecting the two kinds of defects can be generated. The process for adjusting the illumination light amount or the sensitivity of the imaging device or determining the optimal adjustment value when the adjustment value is registered in the memory may be performed by a user or it may be automatically performed by the adjusting device or the control device.

According to the present invention, with only one imaging operation, an image suitable for detecting both irregular defect and the color defect on the surface of the object can be generated and each defect can be detected with high precision. Furthermore, since the image is taken only one time, even when many objects are sequentially to be inspected, very efficient detection can be implemented.

BRIEF DESCRIPTION OF THE DRAWINGS

FIG. 4 shows an explanatory diagram of principles and problems in detecting an irregular defect;

FIG. 5 shows an explanatory diagram of principles in detecting a color defect;

FIG. 6 shows a table summarizing detectable defects and desirable illumination colors in a coaxial incident illumination and an oblique incident illumination;

FIG. 7 shows an explanatory diagram of an example in which setting of a background level is not appropriate;

FIG. 9 shows a table summarizing a result of measured reflection coefficients in a coating layer and a work body;

FIG. 10 shows a table summarizing contents of three methods of generating an image for inspection;

FIG. 11 shows a table summarizing a relation between a combination of light sources and a risk color;

FIG. 14 shows an explanatory diagram of a principle to detect an irregular defect of a work having no coating layer; and FIG. 15 shows an explanatory diagram of principles to detect a color defect of the work having no coating layer.

DETAILED DESCRIPTION OF THE PREFERRED EMBODIMENTS

Figure 1:
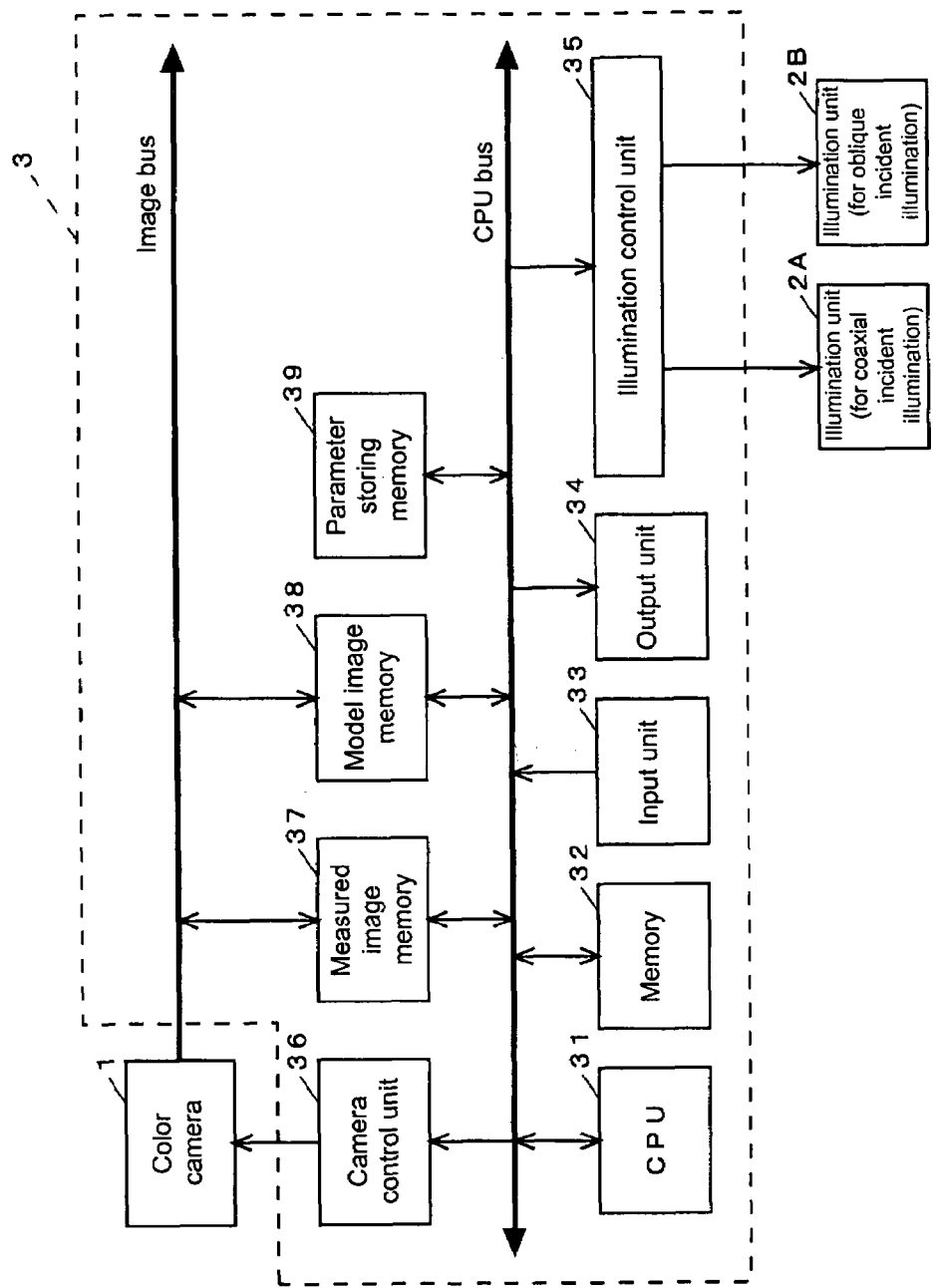
FIG. 1 shows a block diagram of a constitution of a defect inspection system.

FIG. 1 shows an electric constitution of a defect inspection system according to one embodiment of the present invention.

With an inspection object (work) which is a body formed of a colored resin and comprises a transparent coating layer on its surface, this defect inspection system detects a defect generated on a surface of the coating layer or between the coating layer and the work body.

The defect inspection system comprises a color camera 1 serving as an imaging device, two illumination units 2A and 2B, and a measuring unit 3 including a computer for main control. The illumination units 2A and 2B comprise a plurality of LED's as light sources, and the illumination unit 2A performs a coaxial incident illumination to the work and the illumination unit 2B performs an oblique incident illumination.

The measuring unit 3 comprises a CPU 31, a memory 32 storing a program, an input unit 33, an output unit 34, an illumination control unit 35, a camera control unit 36, a measured image memory 37, a model image memory 38, a parameter storing memory 39 and the like. The input unit 33 is provided for inputting a condition or a parameter required for the inspection and comprises a keyboard, a mouse and the like. The output unit 34 is provided for outputting an inspection result and comprises an interface circuit (not shown) to an external device or a monitor device.

The illumination control unit 35 controls ON/OFF and illumination amount of the illumination units 2A and 2B based on an instruction from the CPU 31. The camera control unit 36 controls an operation of the color camera 1 (referred to as the "camera" hereinafter) based on the instruction from the CPU 31 and generates a color image of the inspection object.

In addition, although it is not shown in the drawing, the camera 1 and the illumination units 2A and 2B can be moved by a common positioning mechanism. The CPU 31 controls an operation of the positioning mechanism to position the camera 1 and the illumination units 2A and 2B at predetermined imaging regions and then drives the camera control unit 36 and the illumination control unit 35 to generate the color image for inspection. However, an imaging method for the work is not limited to the above. As another method, the imaging operation may be performed such that a position or a posture of the work is adjusted using a robot arm and the like while the camera 1 and the illumination units 2A and 2B are fixed.

The camera 1 generates digital image data for each color of R, G and B (referred to as the "(each) color image data" hereinafter) according to a drive signal from the camera control unit 36. In addition, in a case where the camera 1 is an analog camera 1, an A/D converter circuit to convert an image signal from the camera 1 to a digital image signal is provided in the measuring unit 3.

A color image from each color image data for the work to be inspected is stored in the measured image memory 37. A color image generated from a non-defective work has been stored in the model image memory 38 as a model image prior to the inspection.

Various kinds of parameters required for the inspection are stored in the parameter storing memory 39. They include a binary threshold value for digitalizing a differential operation image which will be described below, a determining threshold value for determining whether there is a defect or not, an adjustment value of the illumination amount of the illumination units 2A and 2B and the like. The values of these parameters are specified in a teaching mode prior to the inspection like the model image.

Figure 2:
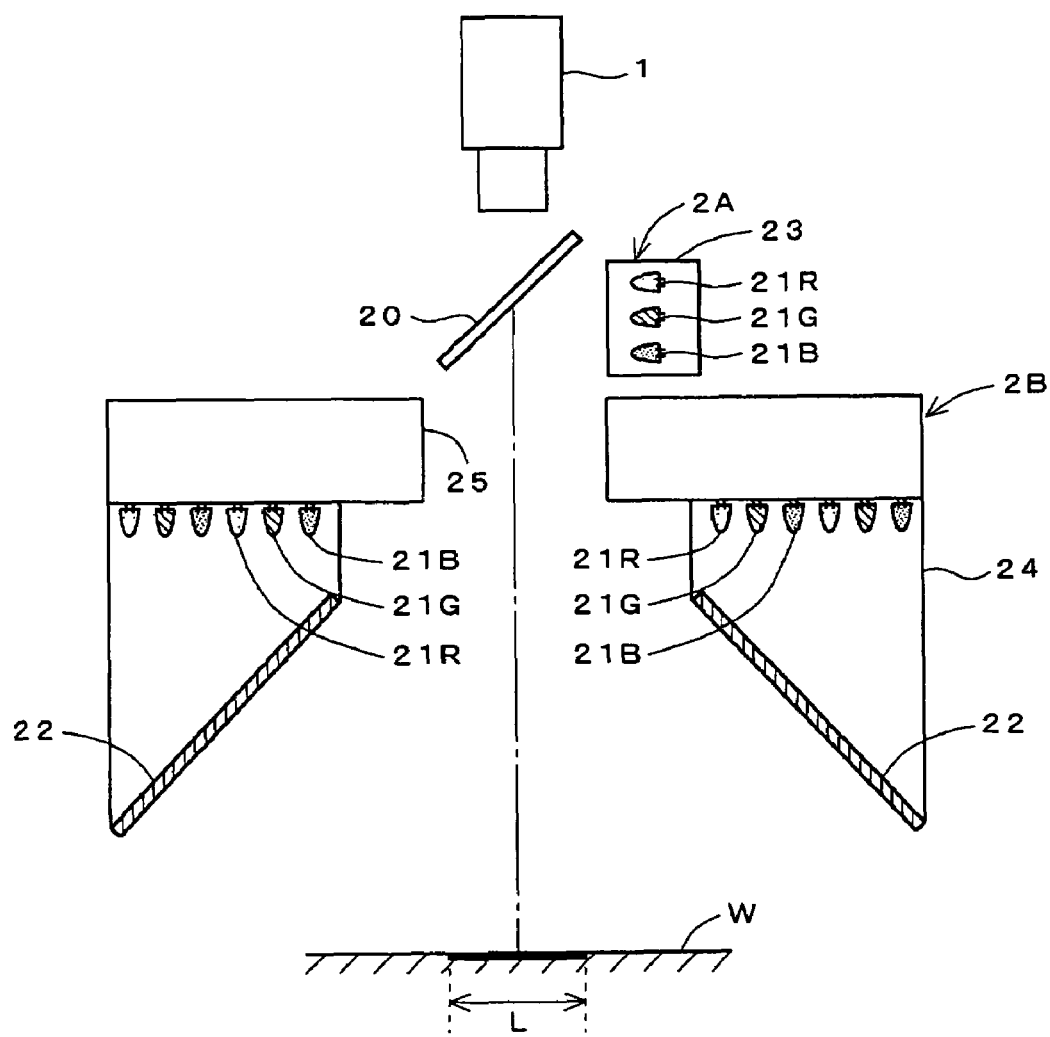
FIG. 2 shows an explanatory diagram of a constitution of an optical system of the defect inspection system.

FIG. 2 shows an optical constitution of the defect inspection system. The camera 1 in this embodiment is arranged above the work W with an optical axis positioned in a vertical direction. A half mirror 20 is provided on the optical axis of the camera 1, and the illumination unit 2A for the coaxial incident illumination is on its side. The illumination unit 2A comprises a case 23 with a predetermined size which houses light sources 21R, 21G and 21B which emit colors R, G and B (they are LED's and referred to as the "red light source 21R", "green light source 21G" and "blue light source 21B" hereinafter), respectively. Each of the light sources 21R, 21G and 21B is arranged such that its optical axis may extend toward the half mirror.

The illumination unit 2B for an oblique incident illumination is provided below the half mirror 20. According to the illumination unit 2B, red light sources 21R, green light sources 21G and blue light sources 21B are arranged in a ring shape in a case 24 comprising an inspection hole 25 for the camera 1 so that their optical axes are arranged in the vertical direction. A lower part of the case 24 is open and a diffusion panel 22 is fitted in the open part. The diffusion panel 22 is set so that a panel surface may be gradually lowered toward the outside of the case 24. Thus, color lights of the R, G and B are mixed in the case 24 and emitted below the inspection hole 25 through the diffusion panel 22.

The camera 1 is arranged such that its optical axis may coincide with a central axis of the inspection hole 25 of the illumination unit 2B. Reference character "L" in the drawing designates a viewing range of the camera 1 set above the work W. A width of the coaxial incident illumination light specified by the half mirror 20, and a width of the oblique incident illumination light specified by the diffusion panel 22 are adjusted so as to correspond to this viewing range L. The camera 1 and the illumination units 2A and 2B are positioned so as to be focused on a predetermined imaging region on the work W by the positioning mechanism to generate the image for the inspection.

In addition, according to the defect inspection system in this embodiment, a plurality of imaging regions are set on the work W prior to the inspection and control amounts for the positioning mechanism can be specified so that the camera 1 and the illumination units 2A and 2B may be focused on each of the regions to be inspected. The control amounts specified here are registered in the parameter storing memory 39 and the like and used at the time of inspection. Since the imaging regions are set all over the surface of the work W, the entire surface of the work W can be inspected.

A description will be made of a defect inspection method in the defect inspection system in detail hereinafter.

Figure 3:
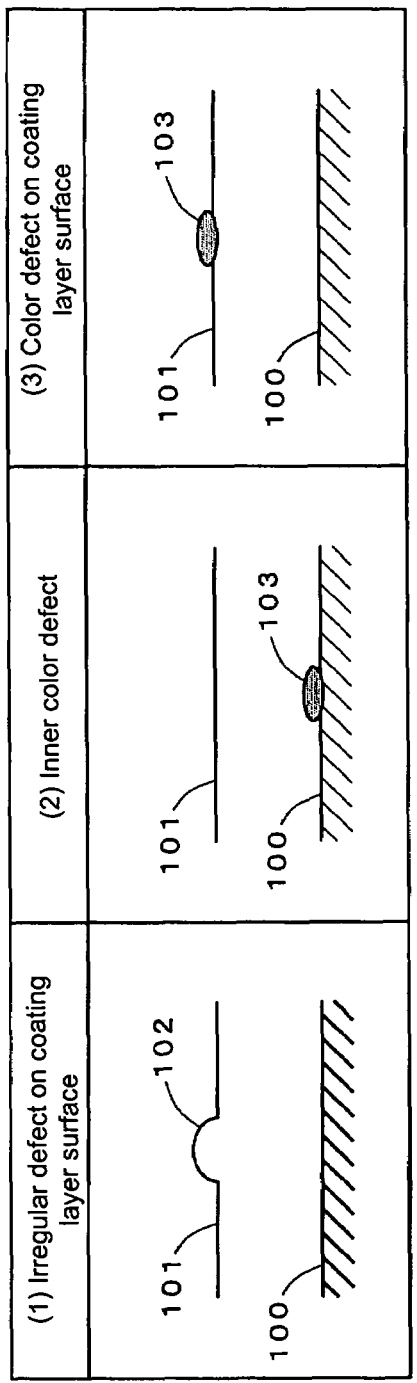
FIG. 3 shows an explanatory diagram of typical defects generated in a work having a coating layer.

FIG. 3 shows typical defects generated in the work. Reference numeral 100 in the drawing designates a body of the work (referred to as the "work body" hereinafter) and reference numeral 101 designates the coating layer.

A defect 102 shown in FIG. 3(1) is an irregular defect on the surface of the coating layer 101, which caused by a defect in a coating process. FIG. 3(2) shows a color defect 103 generated on the surface of the work body 100. The defect 103 is generated when a peripheral coating material is attached and the like at the time of manufacturing process. Meanwhile, FIG. 3(3) shows a color defect generated on the surface of the coating layer 101.

The inventor employed several illuminating methods by which the three kinds of defects can be detected and analyzed their degree of defect detection precision. FIGS. 4 and 5 show the analyzed results.

In addition, it is assumed that this analysis is performed by illuminating and taking an image of the defects in the optical system having the constitution shown in FIG. 2.

FIG. 4 shows the analyzed result regarding the detection of the irregular defect 102 on the surface of the coating layer 101. In FIG. 4, three cases A, B and C are provided according to the work and its defect constitution, and a principle and a problem are shown in each case.

First, in the case A, illumination is adjusted such that diffused reflected amount of the work body 100 may be increased, and the work is irradiated with light from above at a slant (this illumination is referred to as the "obliquely incident illumination" hereinafter). In case there is no irregular 102, this irradiation light passes through the coating layer 101 and then diffused and reflected on the surface of the work body 100. Among the diffused and reflected lights, the light traveling along the optical axis of the camera 1 (that is, the light which travels in the vertical direction) enters the camera 1.

In addition, although the irradiation light is reflected regularly on the surface of the coating layer 101, since the irradiation light is applied to the work obliquely, the regularly reflected light is reflected upward obliquely and it does not enter the camera 1 as will be described below in the case C. Therefore, it is considered that a relatively bright image is provided based on the diffused reflected light generated from the work body 100, at a part having no defect.

Meanwhile, when the irregular defect 102 exists on the surface of the coating layer 101, the light which was reflected from the work body 100 in the vertical direction is diffused by a curved surface of the irregular defect 102. Thus, since the reflected light is prevented from entering the camera 1, the image of the irregular defect 102 becomes darker than the normal part. Therefore, in the case of A, the irregular defect 102 can be detected from a difference in brightness or color of the image.

However, when the curvature of the irregular defect 102 is increased and the surface becomes nearly flat, the reflected light from the work body 100 passes through the irregular defect 102 as shown in a lower part of the case A. In this case, the brightness of the irregular defect 102 is about the same as the other part, so that it is difficult to detect the defect.

In the case of B, the work is irradiated with the light from the direction along the optical axis of the camera 1, that is, the coaxial incident illumination is performed. When the surface of the coating layer 101 is flat without having any irregular defect, it is considered that the regularly reflected light of the irradiation light travels in the vertical direction and enters the camera 1. Meanwhile, when the irregular defect 102 exists on the surface of the coating layer 101, the irradiation light to the irregular defect is reflected in the direction different from the vertical direction and it is highly likely that the light does not enter the camera 1.

Thus, although a bright image can be provided at a part having no irregular defect 102 because of the regularly reflected light from the irradiation range of the irradiation light, the irregular defect 102 appears darker than the normal part because the image of the regular reflected light from the defect part cannot be taken. In addition, when the irregular defect is as small as a wavelength of the light, the regular reflection is not generated and diffused reflection is generated only, so that the image of the regularly reflected light cannot be taken and it appears darker than the normal part. In addition, in the case of the B also, although a part of the irradiation light passes through the coating layer 101 and diffused reflected on the surface of the work body 100 and the diffused and reflected light in the vertical direction enters the camera 1 similar to the case A, since the regularly reflected light from the surface of the coating layer 101 is stronger than that from the surface of the work body in general, it is considered that a difference in brightness between the irregular defect 102 and the normal part can be sufficiently detected. Furthermore, by setting the color of the irradiation light to the color which can suppress an amount of the diffused reflection on the work body 100 (which is a complementary color with the work body 100, for example), an affect of the diffused reflected light can be prevented, and an image which reflects the incident state of the regularly reflected light from the surface of the coating layer 101 with high precision can be generated.

In the case of C, the illumination is adjusted such that the diffused reflection amount of the light from the work body 100 may be reduced, and an image of the regularly reflected light from the coating layer 101 is taken.

Although the work is irradiated obliquely in this method like in the case A, since diffused reflected light from the work body 100 is small and the regularly reflected light from the surface of the coating layer 101 does not enter the camera 1, an image of the part having no irregular defect 102 is relatively dark. Meanwhile, when the irregular defect 102 exists, when the regularly reflected light from the defect travels in the vertical direction, it enters the camera 1. Thus, the image of the irregular defect 102 in this case becomes brighter than the normal part.

However, the irregular defect can be detected in the method shown in the case C only when inclination of the defective surface is in a state in which the regularly reflected light can enter the camera 1. Therefore, in a case where the regularly reflected light from the inclined surface of the irregular defect 102 cannot enter the camera 1 as shown in a lower part, the defect 102 cannot be detected. In addition, when the irregular defect is smaller than the wavelength of the irradiation light, its regularly reflected light is not generated, so that it cannot be detected.

The above analyzed result is summarized as follows. It can be considered that the optimal illumination in view of detecting the irregular defect 102 on the surface of the coating layer 101 is the coaxial incident illumination shown in the case B. In the case B, since not the diffused reflected light from the work body 100 but the regularly reflected light from the surface of the coating layer 101 is used, the brightness of the defect on the image is not varied due to the curvature of the irregular defect unlike the case A. In addition, since the regularly reflected light in the normal state enters the camera 1 and a variation in direction of the regular reflection due to the irregular defect can be detected with high precision, the inclination angle of the defect which can be detected is not limited to a specific range unlike the case C. In addition, even when the irregular defect is too small to be regularly reflected, the irregular defect can be detected from a state in which the regularly reflected light does not enter the camera 1.

Therefore, when the work image is taken with the coaxial incident illumination, a region whose brightness is lower than a predetermined threshold value in the provided image can be detected as the defect.

Next, in FIG. 5, several cases for the color defect 103 generated between the coating layer 101 and the work body 100 and on the surface of the coating layer 101 are provided and a principle of detection is shown for each case.

Cases D and E in the drawing regard the detection of the color defect 103 between the coating layer 101 and the work body 100. The case D shows a case where diffuseness and reflectivity of the work body 100 is relatively high and a color defect which is darker than the work body 100 is generated. Here, when there is no color defect 103, it is considered that diffused reflected light from the work body 100 enters the camera 1 and a relatively bright image is formed like the case A shown in FIG. 4. Meanwhile, when the color defect 103 exists, since the diffused reflected light is prevented at that part, the color defect 103 on the image becomes darker than the normal part.

The case E in the drawing shows a case where the diffuseness and reflectivity of the work body 100 is relatively low and the color defect 103 which is brighter than the work body 100 is generated. Since the incident light to the camera 1 is suppressed at the part where the color defect 103 does not exist, it is considered that the image of the part becomes a relatively dark. However, since the diffused reflected light amount in the color defect 103 is increased as compared with the normal part, the incident light amount to the camera 1 is also increased. As a result, the color defect 103 on the image becomes the brighter than the other part.

Thus, regarding the color defect 103 between the coating layer 101 and the work body 100, an image which reflects the diffused reflected state of the work body 100 can be generated by the oblique incident illumination, preventing the regularly reflected light from the surface of the coating layer 101 from entering the camera 1. Thus, when the defect 103 is darker than the work body 100 or when the defect 103 is brighter than the work body 100, the defect 103 can be detected with the oblique incident illumination.

Cases F and G show a case where the dark color detect 103 exists on the surface of the coating layer 101. In the case of F, similar to the case A, the defect 103 is detected by the oblique incident illumination using a phenomenon in which the diffused reflected light from the work body 100 is prevented by the defect 103. In the case of G, similar to the case B, the defect is detected by the coaxial incident illumination using a phenomenon in which the regularly reflected light is prevented at the defect part.

In both cases F and G, it is considered that an image of the color defect 103 can be generated as a region darker than the other part. However, when the defect has a color having relatively high transparency (yellow, for example), the diffused reflected light from the work body 100 could be transmitted and enter the camera 1 similar to the problem in the case A. Therefore, it is preferable to employ the coaxial incident illumination in the case G.

A case H shows a case where the color defect 103 is brighter than the coating layer 101. However, since a color brighter than the transparent resin layer cannot be specified from a practical viewpoint, it is not necessary to consider the detection principle of the case H.

The analyzed results shown in FIGS. 4 and 5 will be summarized as follows. That is, the coaxial incident illumination is suitable for detecting the irregular defect 102 or the color defect 103 on the coating layer 101, and the oblique incident illumination is suitable for detecting the color defect 102 provided between the coating layer 101 and the work body 100.

According to the defect inspection system shown in FIG. 1, the irregular defect 102 and the color defect 103 on the surface of the coating layer 101 is to be detected using the regularly reflected light of the coaxial incident illumination by the illumination unit 2A and the color defect 103 between the coating layer 101 and the work body 100 is to be detected using the diffused reflected light of the oblique incident illumination by the illumination unit 2B based on the analysis shown in FIGS. 4 and 5.

When the defect is detected with the above two kinds of illuminations, it is preferable to set the color of each illumination and illumination amount appropriately to detect the defect with high precision. A description will be made of preferable setting conditions A and B in this order.

Condition A: Illumination Color

FIG. 6 shows the kind of defect which can be detected in the image under the coaxial incident illumination and the oblique incident illumination and the illumination color suitable for the detection. In addition, as representative examples of the colors of the work body 100, white, gray and yellow are employed and illumination color suitable for each of them and combinations (put in brackets) of the light sources which constitutes the illumination colors (however, in case that the work body 100 is white, since a defect of a color brighter than white cannot be detected, the case is not to be considered).

First, according to the coaxial incident illumination, the irregular defect 102 or the color defect 103 on the surface of the coating layer 101 can be detected as described above. Since the defect is detected using the regularly reflected light from the coating layer 101, it is preferable to use the light whose diffused reflected light from the work body 100 can be prevented.

Thus, the most preferable color is a color having a complementary relation with the color of the work body 100. For example, when the work body 100 is yellow, only the blue light source 21B is lighted to provide a blue illumination which is in the complementary relation.

However, when the work body 100 is achromatic color such as white or gray, since the above principle cannot be applied, even when any color illumination of white, R, G or B is applied, its sensitivity is the same.

Next, the oblique incident illumination is used to detect the color defect 103 provided between the coating layer 101 and the work body 100. However, as shown in the case A and, C in FIG. 4 and in the case G in FIG. 5, the irregular defect 102 or the color defect 103 on the surface of the coating layer 101 can be detected with the oblique incident illumination in some cases.

When the defect of the color darker than the work body 100 is to be detected, it is preferable to use the light whose diffused reflected light amount from the work body 100 is increased as shown in the case D in FIG. 5. More specifically, it is considered to be best that the same color as the work body 100 is used.

For example, when the work body 100 is yellow, it is desirable that the red light source and the green light source are lighted in an intense ratio such as 1:1 to generate a yellow illumination. However, when the work body 100 is the achromatic color such as white or gray, since the above principle cannot be applied, it is preferable that a white illumination is applied.

Meanwhile, when the defect of the color brighter than the work body 100 is to be detected, it is preferable to use the light whose diffused reflected light from the work body 100 is suppressed as shown in the case E in FIG. 5. Thus, similar to the case of the coaxial incident illumination, it is considered to be the best that the color which is in a complementary relation with the color of the work body 100 is used.

When the colors of the two kinds of illuminations are set according to the color of the work body 100 to be inspected based on the condition shown in FIG. 6, the color of the defect can be different from that of the normal part, so that the defect can be detected with high precision. However, since the light source to be used is selected from the three kinds of light sources in practical illumination, the illumination color which can be generated is limited. In addition, according to the oblique incident illumination, since the defect may be darker or brighter than the work body 100, the illumination color cannot be determined uniquely. Therefore, it is necessary to select the combination of the light sources which is suitable for detecting the defect according to its kind with high precision in view of the above condition or the expected defect.

Condition B: Illumination Intensity

As described above, in the image generated in the defect inspection in this embodiment, there are cases where the defect part appears as the region darker than the normal part and brighter than the normal part. Here, when it is assumed that the normal part on the image is a "background" of the defect, a brightness level of the background part (referred to as the "background level" hereinafter) should be appropriate, otherwise the defect cannot be detected with high precision.

Figure 8:
FIG. 8 shows an explanatory diagram of an example in which setting of a background level is appropriate.

FIGS. 7 and 8 show brightness distribution on one line on the image when the image is taken only with the oblique incident illumination. FIG. 7 shows an inappropriate example for the defect detection and FIG. 8 is an appropriate example for the defect detection.

When the image is taken only with the oblique incident illumination, the background level of the generated image is determined by the diffused reflected light amount from the normal part of the work body 100. Therefore, when the amount of the oblique incident illumination is insufficient, the diffused reflected light amount is also not sufficient, so that it is considered that the background level of the image is low. In this case, as shown in FIG. 7A, even when there is a defect darker than the background and its diffused reflected light cannot be generated, since it is not very different from the background level, it is difficult to detect the difference between the background level and the brightness level of the defect part. In addition, even when there is a defect brighter than the background, since an increased amount of the diffused reflected light at the defect part is small, the difference between the brightness level of the defect part and the background level is small as shown in FIG. 7B.

Even when the illumination light amount is increased to raise the background level, in a case where the level is close to a saturated level, the diffused reflected light from the defect brighter than the background is saturated and it becomes difficult to detect the defect as shown in FIG. 7C.

Thus, it is necessary to adjust the background level so that the difference between the brightness level of the defect part and the background level may reach a predetermined value or more in either case where the defect is brighter and darker than the background (the background level satisfying the condition is referred to as the "optimal background level" hereinafter). According to the measurement result by the inventor, the darker defect and the brighter defect can be detected by adjusting the illumination amount such that the background level may become about 0.7 to 0.8 times the saturated level as shown in FIG. 8(1) and 8(2). However, since the optimal background level is varied depending on algorism of the defect determination process, the value shown in FIG. 8 is only one example.

Although it is not necessary to consider the detection of the defect brighter than the background in the image generated with the coaxial incident illumination, since the defect darker than the background is detected, it is preferable that the background level is adjusted in the same condition shown in FIG. 8(1).

In addition, since it is considered that there is a big difference between a regular reflectance on the surface of the coating layer 101 and a diffused reflectance on the work body 100, when the background level of the image is adjusted, it is preferable to adjust the illumination amount such that the brightness of the image corresponding to each illumination may be optimal.

FIG. 9 shows a table showing a result in which the reflection coefficient is measured on the work to be inspected. In this example, when the work body 100 is white, gray and yellow, the reflection coefficient on each surface of the coating layer 101 and the work body 100 is measured. In addition, each measured result is standardized based on the diffused reflectance of the white work body 100. Furthermore, since the white and gray works have the same reflection coefficient for the colors R, G and B, it is shown in a line as common data. Meanwhile, since the yellow work has different reflection coefficient for the colors R, G and B, they are shown respectively.

According to the table, it is clear that the regular reflectance from the coating layer 101 is higher than the diffused reflectance from the work body 100 in any work.

The defect inspection system in this embodiment is set such that the image for inspection can be generated by selecting a method from three methods shown in FIG. 10 in view of the above conditions A and B. The method can be freely changed according to the selection of a user.

According to a method 1 in FIG. 10, an image of the same region to be inspected is sequentially taken two times and the first one is performed by the coaxial incident illumination and the second one is performed by the oblique incident illumination. According to a method 2, the imaging is performed only one time and the coaxial incident illumination and the oblique incident illumination are performed at the same time.

In the methods 1 and 2, the illumination color can be set according to the color of the work body 100 in view of the condition shown in FIG. 6. However, in the case of the coaxial incident illumination, when the regularly reflected light which is sufficiently intense as compared with the diffused reflected light from the work body 100 can be provided, the illumination color may be any color without any consideration of the condition. In addition, when the work body 100 is achromatic color or when it is hardly likely that the defect which appears to be the same color as the work body 100 is generated, the illumination color may be white.

According to the method 1, since the image is generated in each of the two illuminations, the illumination amount can be adjusted such that the image of the optimal background level can be provided in each illumination. However, since it is necessary to perform the imaging two times, it is difficult to implement high-speed processing and the method 1 is not suitable for inspecting many works.

According to the method 2, since the image containing all kinds of defects can be generated at one time, the high-speed processing can be implemented. However, since the brightness of the generated image is the sum of the brightness of the reflected light for two kinds of illuminations, the illumination amount cannot be adjusted based on the optimal background level for each illumination. Therefore, the method 2 is considered to be not suitable for detecting the color defect 103 whose brightness is not very different from that of the work body 100.

Furthermore, when the method 1 is employed, it is preferable that each illumination is separately performed prior to the inspection in a similar manner, and the intensity of the light source is adjusted such that the brightness of the image under each illumination can become the optimal background level. In addition, when the method 2 is employed also, it is preferable that when the illumination amount is adjusted, the coaxial incident illumination and oblique incident illumination are performed respectively and the intensity of the light source is adjusted so that the background level under the respective illuminations may become a predetermined reference value (smaller than the optimal background level).

According to a method 3, the coaxial incident illumination and the oblique incident illumination are performed at the same time like the method 2. However, in this method 3, the same color light source is not used for the two kinds of illuminations. More specifically, when any one of the red light source 21R, green light source 21G and blue light source 21b is used for the coaxial incident illumination, two kinds of the light sources other than the above light source are used for the oblique incident illumination.

For example, when the red light source 21R is used for the coaxial incident illumination, the green light source 21G and the blue light source 21B are used for the oblique incident illumination.

It is confirmed that the general-purpose color camera 1 has a function to receive the colors R, G and B by the corresponding imaging devices, separately. Therefore, according to the method 3, it is considered that among three-color image data which constitutes the color image, the defect on the surface of the coating layer 101 is contained in the color image data (R image data, for example) corresponding to the light source selected in the coaxial incident illumination, and the color defect 103 between the coating layer 101 and the work body 100 is contained in the color image data (G and B image data, for example) corresponding to the light source selected in the oblique incident illumination. Thus, the image required for the inspection can be obtained by imaging one region at a time.

Furthermore, according to this method, it is considered that each color image data reflects the reflected light of either one of the coaxial incident illumination or the oblique incident illumination. Therefore, when the illumination intensity is adjusted, the intensity of the light source is to be adjusted so that each color image data may become the optimal background level while the coaxial incident illumination and the oblique incident illumination are carried out at the same time. Since the condition B can be satisfied by the above setting, the defect can be detected with higher precision.

However, since the combination of the light sources which can be used is limited in this method, there is a problem such that the color which cannot be detected is generated in the oblique incident illumination, especially (this color is referred to as the "risk color" hereinafter). However, in a field for manufacturing the work, it is thought that the color of the defect which is hardly likely to be attached can be anticipated from an ambient environment. In this case, the detection precision of the color defect 103 can be maintained by selecting the light source such that the color which is hardly likely to be attached is as the risk color.

A description will be made of a principle for deriving the risk color hereinafter. In addition, it is assumed that the colors R, G and B have reflection coefficients (r, g and b), respectively in this description.

For example, when the oblique incident illumination using the colors R and B is performed to the work body 100 which is yellow and has reflection coefficients such that (r, g, b)=(1, 1, 0), only the reflection to the red light R is generated in the work body 100. Therefore, the work on the image is red.

Meanwhile, in the case where the red color defect 103 exists, since the reflection coefficients at this part is such that (r, g, b)=(1, 0, 0), only the reflection to the red light R is generated from the above illumination. Thus, since the color defect 103 and the work body 100 have the same color, that is, red, the defect 103 cannot be detected. Namely, when the red light source 21R and the blue light source 21B are selected in the oblique incident illumination, red becomes the risk color.

In addition, when the oblique incident illumination using each of the colors R and G is performed for the above work, reflections to the colors R and B are generated. Thus, the work on the image is yellow which is an actual color. However, when it is assumed that a white defect having reflection coefficients such that (r, g, b)=(1, 1, 1) is attached on the work, reflections to the colors R and G are generated in this defect part similar to the work body 100. As a result, the white defect on the image becomes yellow which is the same as the work body 100, so that it cannot be detected.

Thus, when the red light source 21R and the green light source 21G are selected in the oblique incident illumination, white is the risk color (since yellow is the color of the work body 100, it is considered that yellow does not become the risk color).

Although the actual reflection coefficient for each color in the work body 100 is not simply classified to 1 or 0 and various combinations of the values could be generated, the risk color can be derived from the above principle in any case. That is, the color which is the same color provided when the non-defective work is irradiated and the color in its vicinity become the risk color. When the work on the image is the same color of the original color or close to the original color, white becomes the risk color. Thus, when it is highly likely that the defect color is the derived risk color or close to it, it is preferable that another combination of the light sources is selected.

FIG. 11 shows examples of combinations of the light sources when the above method 3 is used when the work body 100 is white (including silver), yellow, blue, green and red so as to correspond to the risk color. Thus, when such relations are disclosed to the user previously, the user can select the combination of the light sources such that the color of the defect which is most unlikely to be detected may become the risk color in the oblique incident illumination and select the remaining light source for the coaxial incident illumination.

In addition, when the light source is selected, the light source for the coaxial incident illumination can be selected with priority depending on an inspection purpose of the user. In this case, the light source of the light whose diffused reflected light from the work body 100 can be suppressed is selected as the light source for the coaxial incident illumination based on the condition A, and the remaining light sources are selected for the oblique incident illumination. In this case also, when there are plurality of light sources to be selected for the coaxial incident illumination, it is preferable to select the light source under the condition that the risk color of the remaining two kinds of light sources is the most unlikely to be the color of the defect. In addition, although the number of the risk colors is increased, even when the light source for the oblique incident illumination is only one kind, the color defect can be inspected.

Figure 12:
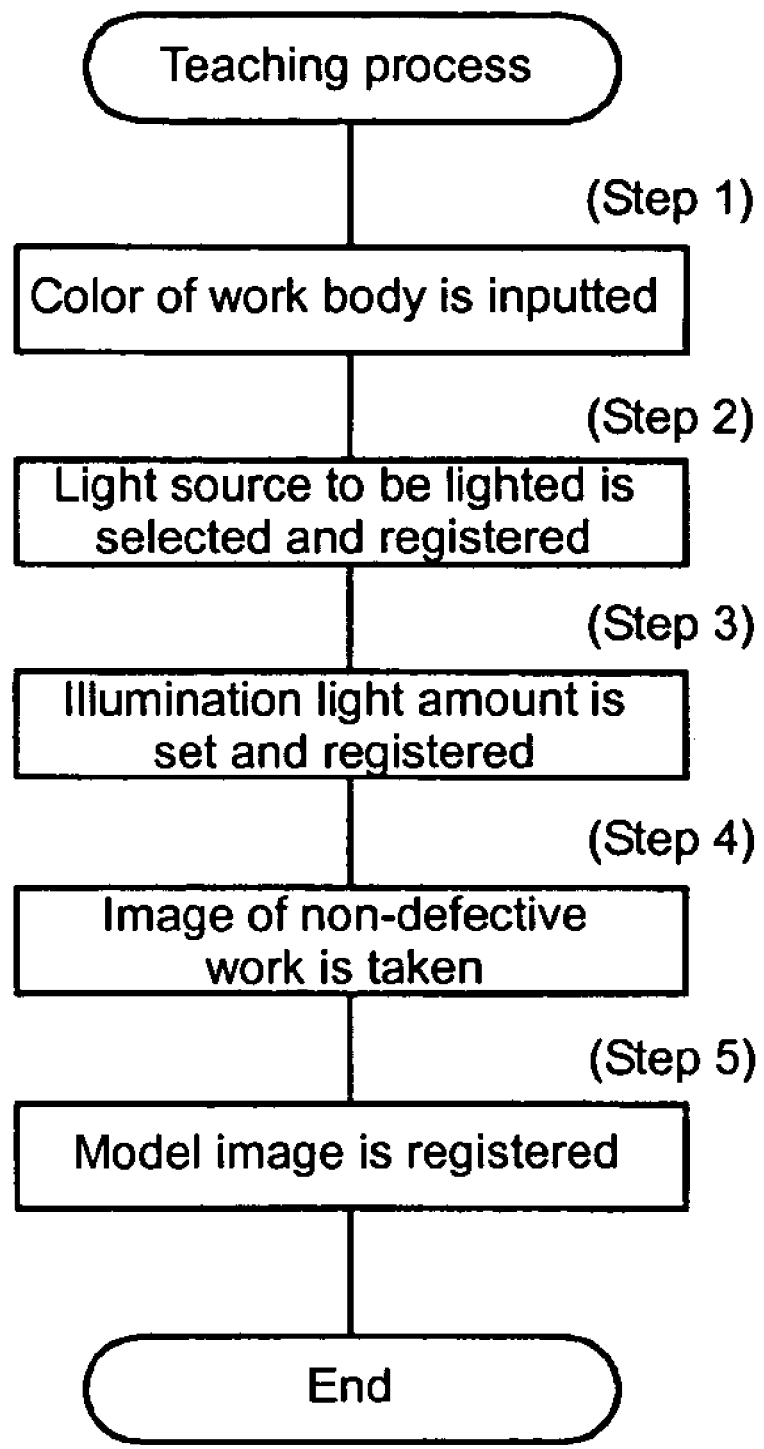
FIG. 12 shows a flowchart of steps of a teaching process.

FIG. 12 shows steps of the teaching process performed for the inspection in the defect inspection system. These steps are considered for the method 3 and step 1 may be omitted in the cases of the methods 1 and 2.

At step 1, the color of the work body 100 is inputted and the inputted color is registered in the parameter storing memory 39. Then, at step 2, an operation to select the light source in the illumination units 2A and 2B is received. The selected result is also stored in the parameter storing memory 39.

Instead of the color input at the step 1, the image of the non-defective work may be taken under a white illumination and the color of the work may be automatically extracted from the obtained image. In this case, the light source selecting process at the step 2 can be automated.

In the case of the method 3, when the table as shown in FIG. 11 is stored in the memory 32 previously, the risk color based on the color of the work body 100 inputted at the step 1 can be displayed on a monitor every combination of the light sources. As a result, the user can select the optimal light source combination referring to the display.

At step 3, the camera 1, and the illumination units 2A and 2B are positioned with respect to the non-defective work and light amounts of the illumination units 2A and 2B are set. When the methods 1 and 2 are performed, the illumination units 2A and 2B are separately driven and the light source selected at the step 2 is lighted and the image is taken under that illumination. Then, it is checked whether the brightness of the work on the generated image is the optimal background level (the predetermined reference level lower than the optimal background level in the method 2) or not. When it is not the optimal background level, the light amounts of the light source is adjusted and the image is taken again. The above operation is repeated until the brightness of the work on the image becomes the optimal background level, and the illumination amount at this point is stored in the parameter storing memory 39.

In the case of the method 3, the adjustment can be performed by carrying out the illuminations at the same time as described above. In addition, instead of the illumination amount, sensitivity of the camera 1 may be adjusted in any method.

Then, at step 4, an image is taken by the same method as that of the actual inspection using the adjusted illumination units 2A and 2B. At step 5, this taken image is stored in the model image memory 38 as the model image.

In addition, when the plurality of imaging regions are set in the work, the steps 4 and 5 are performed every imaging region.

Figure 13:
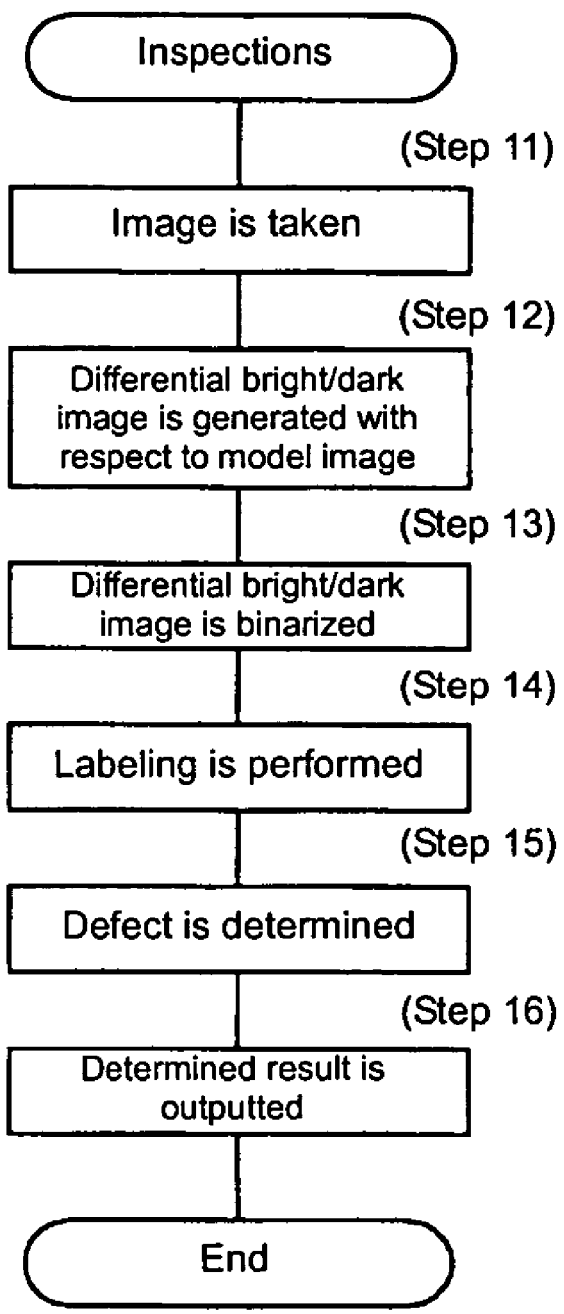
FIG. 13 shows a flowchart of steps at the time of inspection.

FIG. 13 shows inspection steps after the teaching process. This starts from a step 11. To simplify the description, it is assumed that the number of imaging region is one.

At step 11, the camera 1 and the illumination units 2A and 2B are positioned so as to be focused on the imaging region of the work to be inspected and the imaging is performed by the selected method. In this imaging process, the illumination amounts of the illumination unit 2A and 2B are adjusted based on the condition registered at the teaching process. In addition, the image data generated here is stored in the measured image memory 37.

At step 12, the model image is read out from the model image memory 38 and a differential bright/dark image of the image generated at the step 11 is generated with respect to the model image. More specifically, a difference in brightness between corresponding pixels is found every data of the color R, G or B and then the difference values of the data are averaged. Thus, the differential bright/dark data which shows a degree of a difference in color or brightness with respect to the model image can be generated.

At step 13, the differential bright/dark image data provided at the step S12 is binarized with a predetermined binarized threshold value. At step 14, the binarized image is labeled. At these two steps, the region having the color different from the model image is cut out and detected.

At step 15, an area of the each labeled region is measured and the region having a predetermined area or more is recognized as the defect. Thus, based on the recognized result, it is finally determined whether the defect exists or not. When another defect exists, the position or the size of the defect can be measured from the labeled result.

Then, at step 16, the above result is displayed on the monitor or outputted and this processing is completed.

In addition, when the method 1 is carried out, since two images are generated, the steps 13 to 15 are performed every generated image. When the method 3 is carried out, the color image to be inspected and the model image are divided into the color image corresponding to the coaxial incident illumination and the color image corresponding to the oblique incident illumination and the steps 13 to 15 are performed every color image. In this case, the defect detected from the image corresponding to the coaxial incident illumination can be specified as the irregular defect 102 or the color defect 103 on the surface of the coating layer 101. Then, the color defect 103 between the coating layer 101 and the work body 100 can be specified by removing the defect which overlaps with the detected result of the image corresponding to the coaxial incident illumination, from the defect detected from the image corresponding to the oblique incident illumination.

Meanwhile, although the work on which the coating layer is formed is illustrated in the above embodiment, the same inspection can be performed on a work having no coating layer.

In the case of the work having no coating layer, an irregular defect or a color defect on the surface of a work body 100 is to be detected. In this case, as shown in FIGS. 14 and 15, it is considered that the coaxial incident illumination from the illumination unit 2A is suitable for detecting the irregular defect and the oblique incident illumination from the illumination unit 2B is suitable for detecting the color defect.

FIG. 14 shows an example in which the work body 100 having the irregular defect 102 is irradiated with the coaxial incident illumination from the illumination unit 2A. In this case, while the regularly reflected light from the normal part travels toward the camera 1, the regularly reflected light from the irregular defect 102 does not travel toward the camera 1. Thus, the irregular defect 102 on the image becomes a darker region as compared with the other part.

FIG. 15(1) shows an example in which the oblique incident illumination is performed when the dark color defect is generated on the work body 100 having relatively high diffused reflectivity. In this case, since the diffused reflected light is intense at the normal part and that substantial amount of light enters the camera 1, the background part on the image becomes bright. Meanwhile, since the diffused reflection is suppressed at the color defect 103, the diffused reflected light which enters the camera 1 is weak. Thus, the color defect 103 on the image becomes darker than the background part.

FIG. 15(2) shows an example in which the oblique incident illumination is performed when the bright color defect 103 is generated on the work body 100 having relatively low diffused reflectivity. In this case, since the diffused reflected light is weak at the normal part, the background part on the image becomes dark. Meanwhile, since the diffused reflection is enhanced at the color defect 103, the light amount to the camera 1 is increased. Thus, the color defect 103 on the image becomes the brighter region than the other part.

Thus, since the irregular defect 102 on the surface can be detected using the coaxial incident illumination from the illumination unit 2A and the color defect 103 on the surface can be detected using the oblique incident illumination from the illumination unit 2B in the work having no coating layer 101, both defects can be detected using the above methods 1 to 3. In addition, when the method 3 is used, since the risk color is generated in the oblique incident illumination as described in the work having the coating layer 101, it is preferable to select the light source in the illumination units 2A and 2B according to the color of the work or the color of the color defect 103.

What is claimed is:

1. A defect inspection system for inspecting whether a defect is generated or not on a surface of an object to be inspected which is formed of a predetermined material, comprising:

a first illuminating device for illuminating the object to be inspected from a predetermined direction;

a second illuminating device for illuminating the object from an oblique direction with respect to an optical axis of the imaging device;

an imaging device arranged so as to receive a light from the object under an illumination and to thereby generate a color image;

a control device for controlling illumination operations of the first and second illuminating devices and operating the imaging device under illuminations of the first and second illuminating devices;

a detecting device for detecting an irregular defect and a color defect on a surface of the object using a color image generated by the imaging device controlled by the controlling device; and an output device for outputting a result detected by the detecting device, wherein the first and second illuminating devices each comprise three kinds of light sources which emit colors R, G and B, respectively, the control device is configured to light any one of the three kinds of light sources in the first illuminating device and light one or two kinds of light sources which are not lighted in the first illuminating device, in the second illuminating device; and wherein the detecting device is configured to cut the color image generated by the imaging device into an image having a color corresponding to the light source lighted in the first illuminating device, and an image having a color corresponding to the light source lighted in the second illuminating device, and the presence or absence of the irregular defect is configured to be detected using the former image while the presence or absence of the color defect is configured to be detected using the latter image.

2. The defect inspection system according to claim 1, wherein an illumination light color of at least one of the first illuminating device and the second illuminating device is variable.

3. The defect inspection system according to claim 1, further comprising:

an adjusting device for adjusting a light amount of each light source of the first and second illuminating devices or sensitivity of the imaging device for the colors R, G and B individually; and a memory for storing an adjustment value of the adjusting device required for bringing brightness of the image generated by the imaging device to a predetermined target level, wherein the control device applies information stored in the memory to the adjusting device to adjust the light amount of each light source or the sensitivity of the imaging device, prior to inspection.

4. A defect inspection method for inspecting whether a defect is present or not on a surface of an object to be inspected, comprising the steps of:

illuminating the object to be inspected from a predetermined direction using a first illuminating device comprising three kinds of light sources which emit colors R, G and B, respectively;

illuminating the object from an oblique direction with respect to an optical axis of an imaging device using a second illuminating device comprising three kinds of light sources which emit colors R, G and B, respectively;

receiving light from the object under illumination to thereby generate a color image;

controlling illumination operations of the first and second illuminating devices by lighting any one of the three kinds of light sources in the first illuminating device and lighting one or two kinds of light sources which are not lighted in the first illuminating device, in the second illuminating device; and cutting the color image generated by the imaging device into an image having a color corresponding to the light source lighted in the first illuminating device, and an image having a color corresponding to the light source lighted in the second illuminating device, and wherein the presence or absence of an irregular defect is configured to be detected using the former image while the presence or absence of a color defect is configured to be detected using the latter image.

5. The defect inspection method according to claim 4, wherein an illumination light color of at least one of the first illuminating device and the second illuminating device is variable.

6. The defect inspection method according to claim 4, further comprising the steps of:

adjusting a light amount of each light source of the first and second illuminating devices or sensitivity of an imaging device for receiving the colors R, G and B individually; and storing an adjustment value of the adjusting device required for bringing brightness of the image generated by the imaging device to a predetermined target level, wherein a control device applies information to the adjusting device to adjust the light amount of each light source or the sensitivity of the imaging device, prior to inspection.

\* \* \* \* \*